United States Patent [19]

Orth et al.

[11] Patent Number: 4,493,935
[45] Date of Patent: Jan. 15, 1985

[54] PREPARATION OF 1H-PYRROL-2-ACETIC ACID ESTERS

[75] Inventors: Winfried Orth, Hassloch; Werner Fickert, Mannheim, both of Fed. Rep. of Germany

[73] Assignee: Rutgerswerke Aktiengesellschaft, Fed. Rep. of Germany

[21] Appl. No.: 576,202

[22] Filed: Feb. 2, 1984

Related U.S. Application Data

[63] Continuation-in-part of Ser. No. 338,330, Jan. 11, 1982, abandoned.

[30] Foreign Application Priority Data

Nov. 17, 1981 [DE] Fed. Rep. of Germany ....... 3145510

[51] Int. Cl.³ ......................................... C07D 207/337
[52] U.S. Cl. ................................................... 548/562
[58] Field of Search ......................................... 548/562

[56] References Cited

U.S. PATENT DOCUMENTS 3,544,589 12/1970 Orth et al. ............................ 548/562
4,255,335 3/1981 Carson ............................ 548/562 X

FOREIGN PATENT DOCUMENTS 1301313 8/1969 Fed. Rep. of Germany ...... 548/562
1198829 7/1970 United Kingdom ................ 548/562

OTHER PUBLICATIONS

Dehmlow, et al., "Phase Transfer Catalysis", (1980), pp. 69–77, (Monographs in Modern Chemistry, vol. 11).
Organic Synthesis, vol. 60, (1981), p. 69.
Organic Synthesis, vol. 55, (1976), pp. 91 and 96.
CRC Handbook of Chemistry & Physics, 61st, ed., (1980), Weast–Editor, CRC Press, Inc., Boca Raton, Florida.

Primary Examiner—Joseph Paul Brust
Attorney, Agent, or Firm—Charles A. Muserlian

[57] ABSTRACT

A process for the preparation of esters of 1H-pyrrol-2-acetic acids of the formula

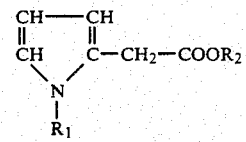

wherein $R_1$ is selected from the group consisting of hydrogen and alkyl of 1 to 4 carbon atoms and $R_2$ is selected from the group consisting of alkyl of 1 to 4 carbon atoms and aralkyl of 1 to 4 alkyl carbon atoms comprising reacting a compound of the formula

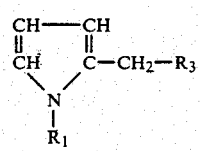

wherein $R_3$ is selected from the group consisting of —CN and

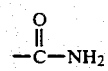

in an aqueous media with a saponification base wherein the saponification base is added gradually to the 1H-pyrrol-2-acetonitrile and/or 1H-pyrrol-2-acetamide to selectively saponify the same to obtain a substantially isomer-free salt of 1H-pyrrol-2-acetic acid, adding alkali metal bicarbonate to the solution to keep the pH of solution at about 10.2 to 10.5 and reacting the salt of 1H-pyrrol-2-acetic acid without isolation and without removal of any water with a solution of an alkylating or aralkylating agent in an organic water-insoluble solvent in the presence of a phase transfer agent to obtain the ester of formula I in excellent yields and purity.

11 Claims, No Drawings

PREPARATION OF 1H-PYRROL-2-ACETIC ACID ESTERS

PRIOR APPLICATION

This application is a continuation-in-part of copending, commonly assigned U.S. patent application Ser. No. 338,330 filed Jan. 11, 1982, now abandoned.

STATE OF THE ART

The 1H-pyrrol-2-acetates of formula I are known to be useful starting materials for the preparation of phenothiazine derivatives which are known to be useful as spasmolytics and antihistamines.

German Pat. No. 1,301,313 describes the preparation of 1H-pyrrol-2-acetic acid esters from the corresponding acetonitriles or acetamides by reacting the latter with alkali metal hydroxide at elevated temperatures in the presence of lower alkylene glycols and their ethers and the water is then distilled from the reaction mixture containing the alkali metal salts of 1H-pyrrol-acetic acid which are then reacted with a solution of an alkyl halide or aralkyl halide in a ketone solvent without isolation. While this process is a "single pot" method, it is expensive since the water from the saponification step must be distilled off and the second step requires a specially prepared solvent mixture. Moreover, the 1H-pyrrol-2-acetic acid esters have a relatively high content of undesired isomeric by-products due to the isomers present in the starting acetonitriles or acetamides.

OBJECTS OF THE INVENTION

It is an object of the invention to provide an economical process for preparing 1H-pyrrol-2-acetic acid esters of formula I from the compounds of formula II in a simple single stage reaction.

It is another object of the invention to produce the esters of formula I in a simple manner free of isomers.

These and other objects and advantages of the invention will become obvious from the following detailed description.

THE INVENTION

The novel process of the invention for the preparation of esters of 1H-pyrrol-2-acetic acids of the formula

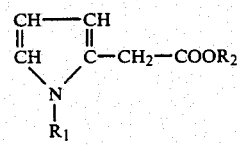

wherein $R_1$ is selected from the group consisting of hydrogen and alkyl of 1 to 4 carbon atoms and $R_2$ is selected from the group consisting of alkyl of 1 to 4 carbon atoms and aralkyl of 1 to 4 alkyl carbon atoms comprises reacting a compound of the formula

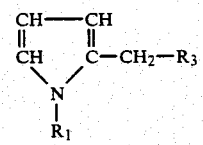

wherein $R_3$ is selected from the group consisting of —CN and

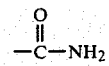

in an aqueous media with a saponification base wherein the saponification base is added gradually to the 1H-pyrrol-2-acetonitrile and/or 1H-pyrrol-2-acetamide to selectively saponify the same to obtain a substantially isomer-free salt of 1H-pyrrol-2-acetic acid, adding alkali metal bicarbonate to the solution to keep the pH of the solution at about 10.2 to 10.5 and reacting the salt of 1H-pyrrol-2-acetic acid without isolation and without removal of any water with a solution of an alkylating or aralkylating agent in an organic water-insoluble solvent in the presence of a phase transfer agent to obtain the ester of formula I.

The process avoids the use of a solubilizing solvent by effecting the addition of the saponification base gradually to the acetonitrile or acetamide of formula II and reacting the resulting salts of 1H-pyrrol-2-acetic acid without isolation from the aqueous reaction mixture with a solution of the alkylating agent or aralkylating agent in a water-insoluble organic solvent in the presence of a phase transfer catalyst. In contrast to German Pat. No. 1,301,313, the saponification step of the process of the invention may be effected without the use of solubilizing organic solvents by heating the aqueous saponification base and compound of formula II whereby the saponification takes place at the organic and aqueous interface with the salt of 1H-pyrrol-2-acetic acid being dissolved in the aqueous phase.

The process of the invention may use the starting 1H-pyrrol-2-acetonitriles in their pure form or their crude form as produced by German Pat. No. 1,301,313, for instance. The crude acetonitriles usually contain as impurity varying amounts of 1H-pyrrol-2-acetamides but these compounds are converted under the process reaction conditions to the corresponding alkali metal 1H-pyrrol-2-acetates. Pure 1H-pyrrol-2-acetamides may also be used as the starting material as well as the impure 1H-pyrrol-2-acetamides which usually contain 1H-pyrrol-2-acetonitrile as impurity.

Examples of suitable bases for the process of the invention are aqueous solutions of alkali metal hydroxides such as sodium hydroxide or potassium hydroxide or alkaline earth metal hydroxides such as calcium hydroxide, barium hydroxide or strontium hydroxide and they are used in at least stoichiometric amounts with respect to the starting acetonitrile or acetamide. Preferably, a 30 to 100% excess of the base is used.

The saponification may be effected by adding all the saponification base at once and then heating the mixture. Preferably, the saponification base is gradually added to the starting 1H-pyrrol-2-acetonitrile and/or 1H-pyrrol-2-acetamide to obtain directly isomer-free salts of 1H-pyrrol-2-acetic acids which can be converted into isomer-free 1H-pyrrol-2-acetic acid esters without the cost of further purification.

The isomeric by-product formed in the production of 1H-pyrrol-2-acetonitrile is 5-methyl-1H-pryrrol-2-carbonitrile which can be saponified to form the corresponding 5methyl-1H-pyrrol-2-carboxylic acid esters. However, it has been found the saponification reaction rates are different for the isomeric nitriles or amides so that the gradual addition of the saponification base to the reaction mixture results in the desired saponification of the 1H-pyrrol-2-acetonitrile to the corresponding acetic acids while the isomeric 5-methyl-1H-pyrrol-2carbonitriles are only hydrolyzed to the corresponding amides under the same reaction conditions.

The ammonia released during the saponification reaction may be simply removed by refluxing the reaction mixture. An alkaki metal bicarbonate is preferably added to the mixture to keep the pH at about 10.2 to 10.5 which is desired for further processing.

The salts of the 1H-pyrrol-2-acetic acids are then reacted with an alkylating agent or aralkylating agent such as the corresponding alkyl halide or alkyl sulfate or aralkyl halide. The reaction temperature will depend on the reactivity of the specific agent. The use of gaseous reagents such as methyl bromide, ethyl bromide or isopropyl bromide require the use of slight pressures to avoid evaporation losses of the alkylating agent.

The alkylating agent or aralkylating agent is added to the aqueous solution of the 1H-pyrrol-2-acetic acid salts in solution in a water-immiscible organic solvent and the esterification is catalyzed by the presence of a phase transfer catalyst to obtain optimum yields up to 100%.

Examples of suitable phase transfer catalysts are phosphonium salts but the preferred catalysts are quaternary ammonium bases such as tetrabutyl quaternary ammonium sulfate. The quaternary ammonium salts may be formed in situ by using a primary amine, secondary amine or tertiary amine which will react with the alkylating or aralkylating agent to form the quaternary ammonium salt. Examples of said amines are alkyl amines such as tripropylamine, dimethylamine, triethylamine and monooctyl amine and cycloalkyl amines such as dicyclohexylamine.

In the following examples there are described several preferred embodiments to illustrate the invention. However, it is to be understood that the invention is not intended to be limited to the specific embodiments.

EXAMPLE 1

920 g (11.5 moles) of 50% sodium hydroxide solution were added dropwise with stirring over one hour at 98° to 100° C. to a mixture of 1200 g (7.7 moles) of 1-methyl-1H-pyrrol-2-acetonitrile and 920 ml of water and the mixture was stirred for 2.5 hours at 98°–100° C. 462 g (5.5 moles) of powdered sodium bicarbonate were added to the mixture to obtain a pH of about 10.5 which was then refluxed for 30 minutes. The mixture was cooled to 70° C. and then 4 liters of toluene and 10 g of tetrabutyl quaternary ammonium hydrogen sulfate were added thereto followed by dropwise addition of 1607 g (12.5 moles) of dimethyl sulfate. The reaction mixture stood at 70° C. for 4 hours and was then cooled. The decanted organic phase was evaporated to dryness under reduced pressure and the residue was rectified. After a small fraction at 95°–118° C. at 19 mbar, there was recovered a major fraction at 118°–120° C. at 19 mbar which was 98–99% of methyl 1-methyl-1H-pyrrol-2-acetate in a yield of 98 to 100% of the theoretical amount. The distillation residue was 1,5-dimethyl-1H-pyrrol-2-carboxamide.

EXAMPLE 2

307 g (3.8 moles) of 50% sodium hydroxide solution were added dropwise over one hour at 98° to 100° C. to a stirred mixture of 400 g (2.57 moles) of 1-methyl-1H-pyrrol-2-acetonitrile and 310 ml of water and the mixture was stirred at 98° to 100° C. for 2.5 hours to effect saponification. Then, 154 g (2.19 moles) of sodium bicarbonate powder were added to the mixture to obtain a pH of about 10.2 which was then refluxed for 30 minutes. 1.3 liters of toluene and 10 g of trioctylamine were added to the mixture followed by even dropwise addition of 536 g (4.24 moles) of dimethyl sulfate over 3 hours at 70° C. The mixture was stirred at 70° C. for 4 hours and was then cooled to room temperature. The decanted organic phase was concentrated at a weak vacuum and the residue was distilled under water jet vacuum. After a small first fraction taken at 95° to 118° C. at 19 mbar, there was recovered a major fraction at 118° to 120° C. at 19 mbar which was 97 to 98% of methyl 1-methyl-1H-pyrrol-2-acetate in a 97-99% theoretical yield. The distillation residue was 1,5-dimethyl-1H-pyrrol-2carboxamide.

EXAMPLES 3 TO 10

Using the procedure of Example 2, 400 g of 1-methyl-1H-pyrrol-2-acetonitrile were saponified and the salts of 1-methyl-pyrrol-2-acetic acid formed were esterified by variation of the base, the alkylating or aralkylating agents and the phase transfer catalysts as indicated in the following Table. The esterification with methyl bromide, ethyl bromide and isopropyl bromide were effected with an over pressure of 1.5 bar. The results of the Examples are reported in the Table.

TABLE

| Example | Base | Alkylating or aralkylating agent | Catalyst | °C. Temperature of esterification excess pressure (bar) | % Yield of theory |
|---|---|---|---|---|---|
| 3 | NaOH | Methyl bromide | Tetrabutylammonium-sulfate | 90° C./1.5 | 96.8 |
| 4 | KOH | Isopropyl bromide | Tetrabutylammonium-sulfate | 90° C./0.8 | 97.5 |
| 5 | NaOH | n-Butyl bromide | Tripropylamine | 100° C./0.0 | 95.2 |
| 6 | NaOH | Dimethylsulfate | Diethylamine | 70° C./0.0 | 97.8 |
| 7 | NaOH | Ethyl bromide | Monooctylamine | 90° C./0.9 | 96.1 |
| 8 | NaOH | Isopropyl bromide | Dicyclohexylamine | 90° C./0.8 | 95.6 |
| 9 | NaOH | Benzyl chloride | Triethylamine | 100° C./0.0 | 95.1 |
| 10 | Ba(OH)$_2$ | n-Butyl bromide | Tributylamine | 100° C./0.0 | 94.1 |

Various modifications of the process of the invention may be made without departing from the spirit or scope thereof and it is to be understood that the invention is intended to be limited only as defined in the appended claims.

What we claim is:

1. A process for the preparation of esters of 1H-pyrrol-2-acetic acids of the formula

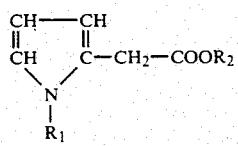

wherein $R_1$ is selected from the group consisting of hydrogen and alkyl of 1 to 4 carbon atoms and $R_2$ is selected from the group consisting of alkyl of 1 to 4 carbon atoms and aralkyl of 1 to 4 alkyl carbon atoms comprising reacting a compound of the formula

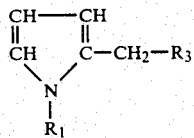

wherein $R_3$ is selected from the group consisting of —CN and —

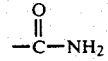

in water with a saponification base wherein the saponification base is added gradually to the 1H-pyrrol-2-acetonitrile and/or 1H-pyrrol-2-acetamide to selectively saponify the same to obtain a substantially isomer free salt of 1H-pyrrol-2-acetic acid, adding alkali metal bicarbonate to the solution to keep the pH of the solution at about 10.2 to 10.5 and reacting the salt of 1H-pyrrol-2-acetic acid without isolation and without removal of any water with a solution of an alkylating or aralkylating agent to introduce the $R_2$ group in an organic water-insoluble solvent in the presence of a phase transfer agent to obtain the ester of formula I.

2. The method of claim 1 wherein the saponification base is an alkali metal hydroxide.

3. The method of claim 1 wherein the saponification base is an alkaline earth metal hydroxide.

4. The process of claim 3 wherein the alkaline earth metal is selected from the group consisting of strontium, barium and calcium.

5. The process of claim 1 wherein the alkylating agent is an alkyl bromide of 1 to 4 carbon atoms.

6. The process of claim 1 wherein the alkylating agent is an alkyl sulfate of 1 to 4 carbon atoms.

7. The method of claim 1 wherein the phase transfer catalyst is a quaternary ammonium salt.

8. The method of claim 1 wherein the phase transfer catalyst is tetrabutyl ammonium sulfate.

9. The process of claim 1 wherein the phase transfer catalyst is a primary amine which is situ reacts with the alkylating agent to form a quaternary ammonium salt.

10. The process of claim 1 wherein the phase transfer catalyst is a secondary amine which in situ reacts with the alkylating agent to form a quaternary ammonium salt.

11. The process of claim 1 wherein the phase transfer catalyst is a tertiary amine which in situ reacts with the alkylating agent to form a quaternary ammonium salt.

* * * * *